United States Patent [19]

Pasquini et al.

[11] 4,430,080
[45] Feb. 7, 1984

[54] SYRINGE ASSEMBLY WITH SNAP-FIT COMPONENTS

[75] Inventors: Richard J. Pasquini, Hackensack, N.J.; Harold Brown, Spring Valley, N.Y.; Alan Kostiuk, deceased, late of Byram Township, Sussex County, N.J., by Barbara Kostiuk, administratrix

[73] Assignee: Becton, Dickinson and Company, Paramus, N.J.

[21] Appl. No.: 386,554

[22] Filed: Jun. 9, 1982

[51] Int. Cl.³ .............................................. A61M 5/00
[52] U.S. Cl. ....................................... 604/240; 604/263
[58] Field of Search .............. 604/242, 243, 241, 240, 604/192, 206, 187, 263

[56] References Cited

U.S. PATENT DOCUMENTS

| | | | |
|---|---|---|---|
| 650,203 | 5/1900 | Stovall | 604/242 |
| 3,491,757 | 1/1970 | Arce | 604/242 |
| 4,240,425 | 12/1980 | Akhavi | 604/192 |
| 4,303,069 | 12/1981 | Cohen | 604/192 |
| 4,334,536 | 6/1982 | Pfleger | 604/263 |

*Primary Examiner*—John D. Yasko
*Attorney, Agent, or Firm*—Richard J. Rodrick

[57] ABSTRACT

A combined syringe and hub assembly in which the syringe comprises a hollow barrel and a slidable plunger therein. The hub comprises a body with an open cavity and a cannula in fluid communication therewith. A mating detent mechanism is provided on the syringe and the hub for connecting same in a snap-fit relationship. This detent mechanism also provides for the connection of the hub to the syringe in a tight fit relationship for an essentially non-separable functional union of the syringe and hub components. A shield is preferably removably connected to the hub and serves to protect the cannula prior to use of the syringe.

9 Claims, 3 Drawing Figures

SYRINGE ASSEMBLY WITH SNAP-FIT COMPONENTS

BACKGROUND OF THE INVENTION

1. Field of the Invention

The present invention relates to a syringe assembly, and more particularly, concerns a combined syringe and hub therefor adapted to meet in a snap-fit relationship, for obtaining a juncture with functional integrity that need not be separable.

2. Description of the Prior Art

Many syringes in use today for a variety of medical or clinical purposes are designed without a needle permanently attached. In these syringes, the barrel may be tapered at its distal end so that the hub of a needle assembly may be attached thereto. One widely known connection of this sort is the LUER-LOK (Registered Trademark of Becton, Dickinson and Company, Paramus, N.J.) connection which allows the needle to be readily attached to the syringe by a twisting movement. This type of attachment of needle to syringe is advantageous inasmuch as different size needles may be attached to many of the different types of syringes which provide the LUER-LOK connection. Other screw-type closures have been known for making this connection between needle and syringe.

Although the twist or screw-type closures between needle and syringe perform more than satisfactorily, ways to improve performance of the closure and minimize expense of fabrication are still being sought. The present invention is directed toward the achievement of these two sought after objectives.

SUMMARY OF THE INVENTION

The combination of the present invention includes a syringe and a hub connected thereto. Comprising the syringe are a hollow barrel and slidable plunger means inside the barrel. The hub is comprised of a body with an open cavity therein and a cannula in fluid communication with the cavity. Mating detent means on the syringe and the hub connects same in a snap-fit relationship. This detent means also preferably contributes to a permanent connection between hub and syringe.

In a preferred embodiment of the present invention, a syringe and a hub are permanently connected to each other, with a shield being removably connected to the hub. The syringe includes a hollow barrel being substantially cylindrically shaped and having a proximal end and a distal end with the distal end having a smaller diameter than the diameter of the remainder of the barrel. Slidable plunger means in the barrel extends from the proximal end of the barrel. A continuous ring or a plurality of protuberances is spaced substantially equally apart around the outer periphery of the distal end of the barrel. The hub is comprised of a body with an open cavity therein and a cannula extending from the body in fluid communication with the cavity. This cavity is generally sized to receive the distal end of the barrel therein. An annular groove is formed in the body around the periphery of the cavity with the protuberances on the syringe being positioned therein. All of the protuberances and the annular groove are shaped to permit a tight fit between the hub and the barrel. The shield is substantially hollow, covers the cannula and is removably connected to the body of the hub.

In accordance with the principles of the present invention, a number of advantages are offered over the known needle to syringe connection mechanisms. For example, the present invention provides a positive snap-action connection compared to the twist or screw-type closure. In addition, the components of the present invention are assembled by a push action along an axial direction thereby eliminating any twist or screw action. Similarly, the shield of the present invention may be disassembled from the hub by the same type of axial force oppositely applied to separate those components. Moreover, the elements which are included on the syringe, hub and shield components of the present invention are easy to mold in high-quantity production runs and should require less sophisticated fabrication equipment than the twist or screw-type closures.

DETAILED DESCRIPTION

Figure 1:
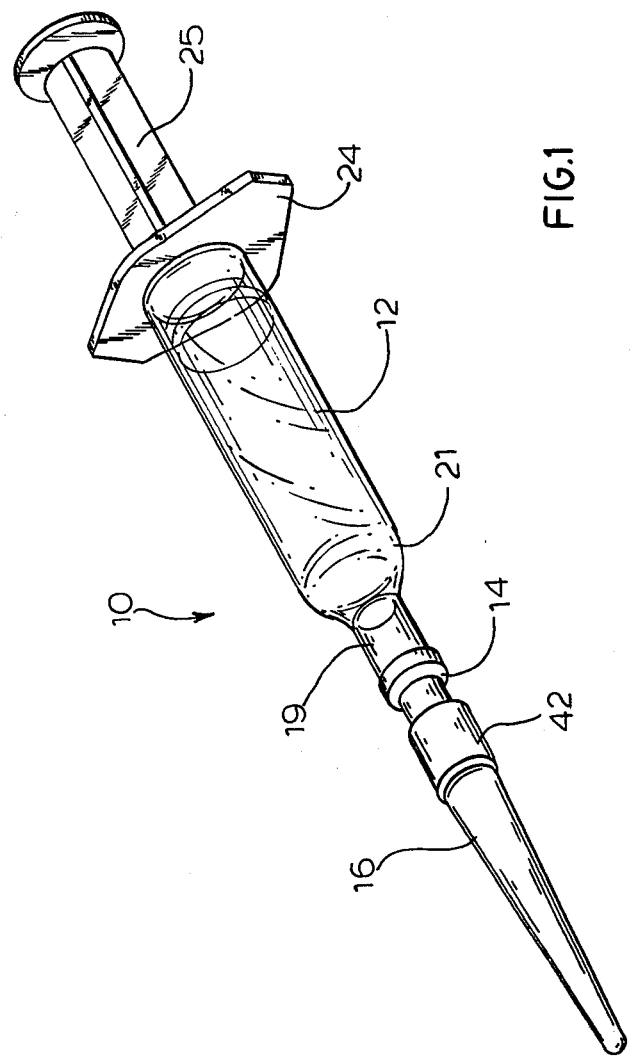
FIG. 1 is a perspective view illustrating the preferred embodiment of the syringe assembly of the present invention with the components thereof assembled.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Adverting to the drawings, and FIG. 1 in particular, there is illustrated a syringe assembly 10 as it may appear with all its preferred components in an assembled condition. Syringe assembly 10 includes three primary components: a syringe 12, a hub 14 and a shield 16.

Figure 2:
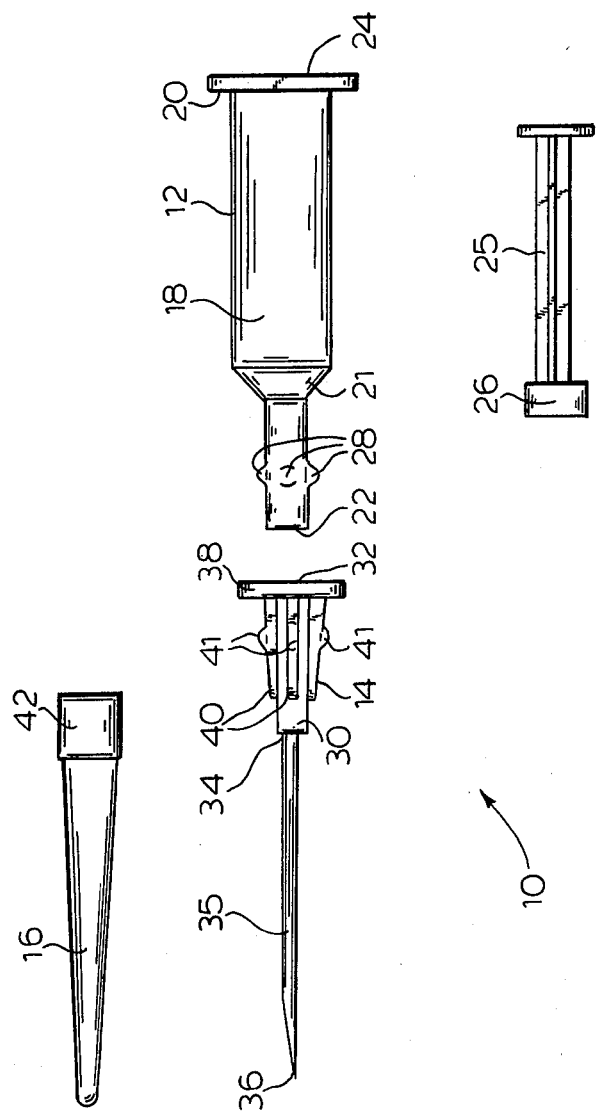
FIG. 2 is an exploded plan view illustrating the individual components of the syringe assembly of FIG. 1.

Referring now to FIG. 2, taken in conjunction with FIG. 1, it can be seen that syringe 12 comprises a hollow barrel 18 which is substantially cylindrically shaped. Barrel 18 has a distal end 19 and a proximal end 20. It can be seen that distal end 19 has a diameter which is smaller than the diameter of the remainder of the barrel. A tapered surface 21 provides for a smooth transition to the smaller diameter of distal end 19. An opening 22 is provided in the distal end of the syringe barrel, as more clearly seen by referring to FIG. 3. Also, proximal end 20 of the barrel has an opening (not shown) communicating with the hollow interior of the barrel. A flange 24 is positioned at proximal end 20 to assist the user in grasping the syringe during use. A slidable plunger 25 is assembled inside barrel 18 through the opening at proximal end 20. Plunger 25 generally includes a piston 26 which provides a liquid-tight, but slidable, surface against the inside wall of barrel 18, as is commonly known in the field of syringes.

Figure 3:
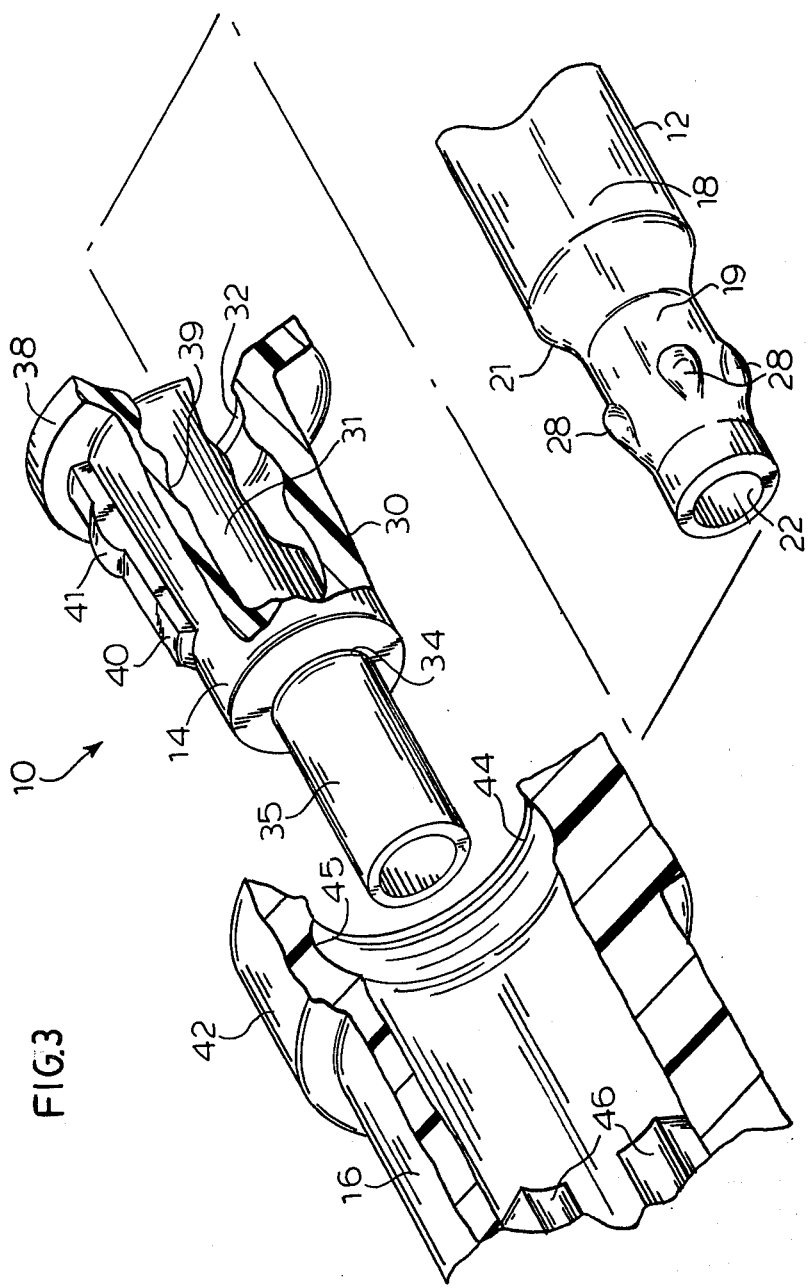
FIG. 3 is an exploded, enlarged perspective view of the syringe assembly of FIG. 1 illustrating, in partial cut-away, the details of the components of the syringe assembly.

By referring to FIGS. 2 and 3, it can be seen that distal end 19 of the syringe barrel includes a plurality of protuberances 28 spaced substantially equally apart around the outer periphery of the distal end. In the embodiment being described, there are four equally spaced protuberances, however, the number may be varied according to performance requirements. Protuberances 28 are preferably smooth-shaped elements so as to enable hub 14 to be slid thereover as will hereinafter be discussed. It should also be pointed out that the protuberances can be designed to make it easy to slide the hub thereover for attachment purposes but difficult to readily remove the hub.

Hub 14 includes a body 30 with a cavity 31 therein communicating with an opening 32 at one end thereof. At the other end of body 30 is another opening 34 into which cannula 35 is positioned. This cannula is preferably a rigid, hollow needle having a sharp point 36 at its far end. Cannula 35 is thereby placed in fluid communication with cavity 31. For ease of handling and manipulation, a flange 38 surrounds opening 32. Cavity 31 is generally sized to receive distal end 19 of the syringe barrel therein for connection purposes. Just interior to opening 32 is an annular groove 39 indented into the wall of body 30 around the periphery of cavity 31. Groove 39 is shaped and positioned so as to receive protuberances 28 therein when the hub is connected to the distal end of the syringe barrel. It is preferred that groove 39 have a smooth surface so as to facilitate the positioning of the protuberances therein in snap-fit fashion. This will also contribute to maintaining the hub in a very tight fit relationship on the syringe barrel. It is appreciated that while the preferred embodiment being described includes an annular groove for the receipt of the protuberances, other indentation means fall within the purview of the present invention. For example, other indentation means may include a plurality of recesses formed in body 30 around cavity 31 arranged to coincide in alignment with the protuberances on the distal end of the syringe barrel. Such an arrangement would serve the same purpose as the annular groove found in the embodiment being described.

If cannula shield 16 is expected to be utilized in conjunction with the present invention, it is preferred that hub 14 include a mechanism to allow shield 16 to be removably connected to the body of the hub. To this end, body 30 preferably includes a plurality of ridges 40 longitudinally oriented around the outer periphery of the hub body. These ridges will assist in guiding cannula shield 16 into position onto the hub. To maintain shield 16 in position on hub 14, each ridge 40 includes a raised protuberance 41 thereon. Protuberances 41 on the hub are similar to protuberances 28 on the distal end of the syringe barrel. Protuberances 41 are also preferably smooth-shaped and are intended to allow the cannula shield to be snap-fit onto the hub.

Cannula shield 16 is preferably a substantially hollow member, elongate in shape, and serving to cover cannula 35 and protect same before the syringe assembly is used. Shield 16 includes a connection end 42 which includes an opening 44 through which cannula 35 enters when the shield is slid into position onto the hub. Just inside opening 44 is an annular groove 45 recessed into the wall of the connection end of the shield. Groove 45 is designed to receive protuberances 41 therein when the shield is slid onto the hub. It is preferred that groove 45 be smoothly shaped so as to facilitate a snap-fit connection of the components. Shield 16 also includes a plurality of ribs 46 around the interior surface thereof. When the shield is slid onto the hub, ribs 46 contribute to the application of axial forces to the hub during assembly. It is also appreciated that other indentation means may be employed inside the shield in order to facilitate the snap-fit features of the present invention.

To assemble the syringe assembly of the present invention prior to use, cannula shield 16 is slid in an axial direction over cannula 35 onto hub 14. This axial sliding action continues until protuberances 41 are snap-fit into annular groove 45 inside shield 16. Then, this composite structure of shield and hub is also axially slid over distal end 19 of syringe barrel 18. This sliding action continues until protuberances 28 are snap-fit into groove 39 inside the hub. The aforementioned protuberances and grooves provide a detent mechanism for maintaining the respective components in an assembled condition, such as illustrated in FIG. 1.

When it is time to use the syringe assembly of the present invention as assembled, the operator merely withdraws shield 16 from the assembly by applying an axially directed force to separate the shield from the hub. The shield groove-hub protuberance interface may be designed so that the shield is readily removable from the hub, whereas the hub, in turn, cannot be readily removed from the syringe barrel.

While many materials may be utilized in manufacturing the components of the present invention, it is preferred that plastic be the material of choice. However, the needle cannula is preferably made of metal in most circumstances.

Thus, the present invention provides a syringe assembly in which the components thereof are assembled in a snap-fit fashion merely by pushing the components together. Similarly, the shield of the syringe assembly may be separated by merely pulling it in an axial direction rather than having to twist or unscrew it.

What is claimed is:

1. In combination, a syringe said shield and a hub connected thereto, said syringe comprising a hollow barrel having a proximal end and a distal end, a slidable plunger in said barrel extending from the proximal end of said barrel, and a plurality of protuberances spaced around the outer periphery of the distal end of said barrel, said hub comprising a body with an open cavity therein and a cannula extending from said body in fluid communication with said cavity, said cavity being generally sized to receive the distal end of said barrel therein, said body having indentation means therein around the periphery of said cavity with said protuberances being positioned therein, said combination further including a substantially hollow shield covering said cannula removably connected to said body, said hub including a plurality of protuberances spaced around its outer periphery and said shield including indentation means for receiving said hub protuberances therein, said hub protuberances and said shield indentation means being shaped to permit the ready removal of said shield from said hub.

2. The combination of claim 1 wherein said barrel is substantially cylindrically shaped.

3. The combination of claim 2 wherein the diameter of said barrel at the distal end is smaller than the remainder of said barrel with said barrel protuberances being located around said smaller diameter.

4. The combination of claim 1 wherein said barrel protuberances are spaced substantially equally apart.

5. The combination of claim 1 wherein said body indentation means is an annular groove in said body around said cavity.

6. The combination of claim 1 wherein said body indentation means is a plurality of recesses around said cavity arranged to coincide in alignment with the protuberances on said barrel.

7. The combination of claim 1 wherein said syringe, said shield and said hub are made of plastic.

8. The combination of claim 1 wherein said shield indentation means is an annular groove.

9. The combination of claim 8 wherein the shield groove-hub protuberance interface and the hub indentation means-barrel protuberance interface, respectively, permit the shield to be removed from said hub with less force than that required to remove said hub from said barrel.

* * * * *

UNITED STATES PATENT AND TRADEMARK OFFICE
CERTIFICATE OF CORRECTION

PATENT NO. : 4,430,080

DATED : February 7, 1984

INVENTOR(S) : Richard J. Pasquini, Harold Brown and Alan Kostiuk, deceased

It is certified that error appears in the above-identified patent and that said Letters Patent are hereby corrected as shown below:

Column 4, Line 33, Claim 1

Delete "said shield"

*Signed and Sealed this*

*Twenty-fourth* Day of *April 1984*

[SEAL]

*Attest:*

GERALD J. MOSSINGHOFF

*Attesting Officer*     *Commissioner of Patents and Trademarks*